United States Patent
Bhat et al.

(10) Patent No.: US 10,428,109 B1
(45) Date of Patent: Oct. 1, 2019

(54) PROCESS FOR THE PREPARATION OF 1,5-BENZOTHIAZEPINE COMPOUNDS

(71) Applicant: ELOBIX AB, Göteborg (SE)

(72) Inventors: Ganapati G. Bhat, Bangalore (IN); Johnson M. Coutinho, Bangalore (IN); Mikael Dahlström, Mölndal (SE); Michael Lofthagen, Stockholm (SE); Akinori Tatara, Kanagawa (JP)

(73) Assignee: Elobix AB, Göteborg (SE)

( * ) Notice: Subject to any disclaimer, the term of this patent is extended or adjusted under 35 U.S.C. 154(b) by 0 days.

(21) Appl. No.: 16/370,753

(22) Filed: Mar. 29, 2019

Related U.S. Application Data

(63) Continuation of application No. PCT/SE2019/050208, filed on Mar. 8, 2019.

(30) Foreign Application Priority Data

Mar. 9, 2018 (IN) .............................. 201811008692
Apr. 23, 2018 (SE) .................................. 1850474-6

(51) Int. Cl.
| | | |
|---|---|---|
| *C07D 281/02* | (2006.01) | |
| *C07D 281/10* | (2006.01) | |
| *C07K 5/062* | (2006.01) | |
| *A61K 31/554* | (2006.01) | |
| *A61P 3/06* | (2006.01) | |

(52) U.S. Cl.
CPC ...... *C07K 5/06026* (2013.01); *C07B 2200/13* (2013.01)

(58) Field of Classification Search
CPC .. C07D 281/02; C07D 281/10; A61K 31/554; A61P 3/06
USPC ...................................... 514/211.09; 540/552
See application file for complete search history.

(56) References Cited

U.S. PATENT DOCUMENTS

| | | | |
|---|---|---|---|
| 7,192,946 B2 * | 3/2007 | Starke .................. | C07D 417/12 514/211.09 |
| 2017/0143738 A1 | 5/2017 | Ando | |
| 2017/0143783 A1 | 5/2017 | Ando | |

FOREIGN PATENT DOCUMENTS

| | | |
|---|---|---|
| WO | WO 2001/66533 | 9/2001 |
| WO | WO 2002/050051 | 6/2002 |
| WO | WO 2003/020710 | 3/2003 |
| WO | WO 2003/022286 | 3/2003 |
| WO | WO 2003/022825 | 3/2003 |
| WO | WO 2003/091232 | 11/2003 |
| WO | WO 2003/106482 | 12/2003 |
| WO | WO 2004/089350 | 10/2004 |
| WO | WO 2012/064266 | 5/2012 |
| WO | WO 2014/174066 | 10/2014 |
| WO | WO 2016/062848 | 4/2016 |

OTHER PUBLICATIONS

PCT Invitation to Pay Fees, Partial Search Result and Provisional Opinion in International Appln. No. PCT/SE2019/050208, dated May 15, 2019, 11 pages.
SE Search Report in Swedish Appln. No. 1850474-6, dated Oct. 11, 2018, 3 pages.

* cited by examiner

*Primary Examiner* — Brenda L Coleman
(74) *Attorney, Agent, or Firm* — Fish & Richardson P.C.

(57) ABSTRACT

The present invention relates to a process for the preparation of certain 1,5-benzothiazepine compounds, and in particular to a process for the preparation of elobixibat. The process can be carried out under mild and safe conditions and may be used to prepare elobixibat on an industrial scale. The invention also relates to a process for the preparation of a crystalline monohydrate of elobixibat.

20 Claims, No Drawings

PROCESS FOR THE PREPARATION OF 1,5-BENZOTHIAZEPINE COMPOUNDS

The present invention relates to a process for the preparation of certain 1,5-benzothiazepine compounds, and in particular to a process for the preparation of elobixibat. The process can be carried out under mild and safe conditions and may be used to prepare elobixibat on an industrial scale. The invention also relates to a process for the preparation of a crystalline monohydrate of elobixibat.

BACKGROUND

Elobixibat (1,1-dioxo-3,3-dibutyl-5-phenyl-7-methylthio-8-(N—{(R)-1'-phenyl-1'-[N'-(carboxymethyl)-carbamoyl]methyl}carbamoylmethoxy)-2,3,4,5-tetrahydro-1,5-benzothiazepine) is an ileal bile acid transporter (IBAT) inhibitor and can be used in the treatment of prevention of dyslipidemia (WO 02/50051), constipation (WO 2004/089350) and liver diseases such as cholestatic liver diseases and non-alcoholic steatohepatitis (WO 2012/064266).

The ileal bile acid transporter is located in the small intestine, particularly in the ileum, and is responsible for mediating the uptake of bile acids from the small intestine to the liver, as part of a process known as enterohepatic circulation. Typically, approximately 95 percent of bile acids are recirculated via the IBAT to the liver, with the remaining 5 percent being secreted to the colon. By suppressing the reabsorption of bile acids from the small intestine to the liver, an increased amount of bile acids is secreted to the colon. The higher concentration of bile acids in the colon in turn leads to an increased secretion of electrolytes and water, resulting in a softening of the stool and higher motility in the large bowel. As an inhibitor of the ileal bile acid transporter, elobixibat may therefore be used in the treatment of constipation.

The preparation of elobixibat and several related 1,5-benzothiazepine compounds is disclosed in WO 02/50051. The preparation of elobixibat comprised a large number of consecutive steps, and involved several reagents that are less desirable from an environmental or safety perspective. The purification of the final product (elobixibat) and several of the intermediate products required preparative chromatography, which works well for small scale synthesis but which is less suitable for industrial scale production.

Several stable crystal modifications of elobixibat have been disclosed in WO 2014/174066 and WO 2016/062848, including crystal modification IV of elobixibat. However, the methods for obtaining the hydrate and anhydrate forms described in these documents are not optimized for production on an industrial scale.

Thus, there is a need for an improved process for the preparation of elobixibat, or a crystalline monohydrate thereof such as crystal modification IV. Such process should make it possible to produce elobixibat on an industrial scale, and in higher yields and higher purity than previously described processes.

DETAILED DESCRIPTION OF THE INVENTION

The present invention provides an improved process for the preparation of elobixibat and closely related 1,5-benzothiazepine compounds.

In a first aspect, the invention relates to a process for the preparation of a compound of formula (I):

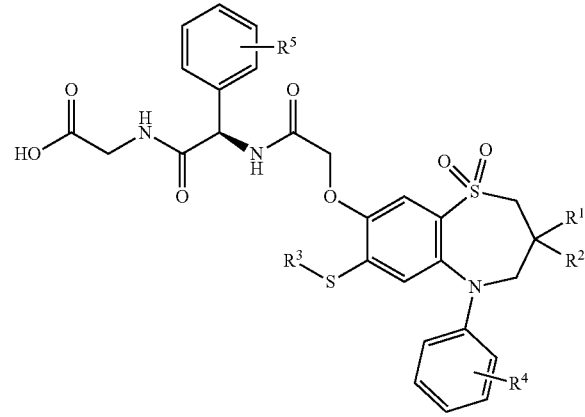

(I)

or a pharmaceutically acceptable salt thereof,
wherein
$R^1$ and $R^2$ are each independently $C_{1-4}$ alkyl;
$R^3$ is $C_{1-4}$ alkyl;
$R^4$ is selected from the group consisting of hydrogen, hydroxy, halo, nitro, cyano and $C_{1-4}$ alkyl; and
$R^5$ is selected from the group consisting of hydrogen, hydroxy, halo, nitro, cyano and $C_{1-4}$ alkyl;
comprising reacting a compound of formula (II):

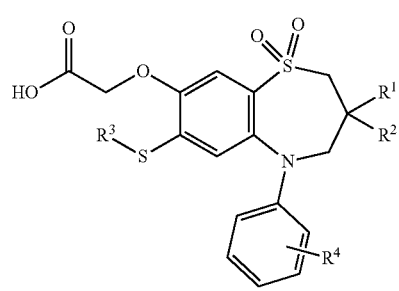

(II)

wherein $R^1$ to $R^4$ are as defined above,
with a compound of formula (III):

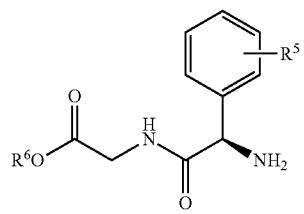

(III)

wherein
$R^5$ is as defined above; and
$R^6$ is a suitable protecting group;
to obtain a compound of formula (IV):

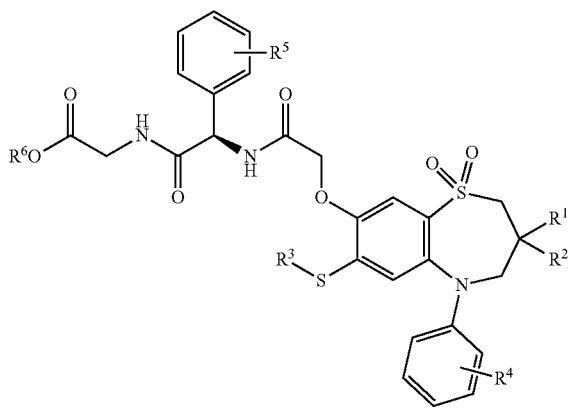

(IV)

and deprotecting said compound of formula (IV) to obtain the compound of formula (I).

As used herein, the term "halo" refers to fluoro, chloro, bromo and iodo.

As used herein, the term "$C_{1-4}$ alkyl" refers to a straight or branched alkyl group having from 1 to 4 carbon atoms. Examples of $C_{1-4}$ alkyl include methyl, ethyl, n-propyl, isopropyl, n-butyl, isobutyl, sec-butyl and tert-butyl.

As used herein, the term "$C_{1-4}$ haloalkyl" refers to a $C_{1-4}$ alkyl group as defined above, but wherein at least one of the hydrogen atoms has been replaced with halogen. Examples of $C_{1-4}$ haloalkyl include fluoromethyl, difluoromethyl, trifluoromethyl.

As used herein, the term "protecting group" refers to a temporary substituent which protects a potentially reactive functional group from undesired chemical transformations. Examples of such protecting groups include esters of carboxylic acids, such as alkyl esters and silyl esters of carboxylic acids. The field of protecting group chemistry has been extensively reviewed; see e.g. Wuts, P. G. M. and Greene, T. W., *Greene's Protective Groups in Organic Synthesis*, 4$^{th}$ ed.; John Wiley & Sons, Hoboken, 2006.

As used herein, the term "about" refers to a value or parameter herein that includes (and describes) embodiments that are directed to that value or parameter per se. For example, description referring to "about 20" includes description of "20." Numeric ranges are inclusive of the numbers defining the range. Generally speaking, the term "about" refers to the indicated value of the variable and to all values of the variable that are within the experimental error of the indicated value (e.g., within the 95% confidence interval for the mean) or within 10 percent of the indicated value, whichever is greater.

In a preferred embodiment, the invention relates to a process for the preparation of a compound of formula (I), wherein $R^1$ and $R^2$ are each n-butyl. In another preferred embodiment, the invention relates to a process for the preparation of a compound of formula (I), wherein $R^3$ is methyl. In another preferred embodiment, the invention relates to a process for the preparation of a compound of formula (I), wherein $R^4$ is hydrogen. In yet another preferred embodiment, the invention relates to a process for the preparation of a compound of formula (I), wherein $R^5$ is hydrogen. In a most preferred embodiment, the invention relates to a process for the preparation of a compound of formula (I) wherein $R^1$ and $R^2$ are each n-butyl, $R^3$ is methyl and $R^4$ and $R^5$ are each hydrogen (i.e. elobixibat).

In the first step of the claimed process, a carboxylic acid of formula (II) is subjected to a condensation reaction with an O-protected peptide of formula (III), preferably in the presence of a coupling reagent and a suitable base.

The compound of formula (III) is preferably used in slight excess of the compound of formula (II), more preferably in an amount of about 1.0 to about 1.3 equivalents with respect to the compound of formula (II), most preferably in an amount of about 1.2 equivalents with respect to the compound of formula (II).

$R^6$ in formula (III) is a suitable protecting group, more preferably a protecting group that may be removed under acidic conditions. In a preferred embodiment, $R^6$ is selected from the group consisting of $C_{1-4}$ alkyl and trisubstituted silyl. More preferably, $R^6$ is tert-butyl or trimethylsilyl, and most preferably tert-butyl.

Examples of suitable coupling reagents include carbodiimides such as dicyclohexylcarbodiimide and diisopropylcarbodiimide; N,N'-carbonyldiimidazole; O-(benzotriazole-1-yl)-N,N,N',N'-tetramethyluronium tetrafluoroborate (TBTU); and O-(benzotriazol-1-yl)-N,N,N',N'-tetramethyluronium hexafluorophosphate (HBTU). In a preferred embodiment, the coupling reagent is a carbodiimide or O-(benzotriazole-1-yl)-N,N,N',N'-tetramethyluronium tetrafluoroborate, and most preferably O-(benzotriazole-1-yl)-N,N,N',N'-tetramethyluronium tetrafluoroborate.

The coupling reagent can be used in slight excess of the compound of formula (II), most preferably in an amount of about 1.0 to about 1.3 equivalents with respect to the compound of formula (II).

Examples of suitable bases include tertiary alkyl amines such as triethylamine; and aromatic amines such as pyridine and 2,6-lutidine. In a preferred embodiment, the base is 2,6-lutidine.

The base is preferably used in excess of the compound of formula (II), preferably in an amount of about 1.5 to about 4.0 equivalents, more preferably in an amount of about 2.5 to about 3.5 equivalents with respect to the compound of formula (II).

Suitable solvents for the condensation reaction include ethers such as tetrahydrofuran, dioxane, cyclopentyl methyl ether and 1,2-dimethoxyethane; esters such as ethyl acetate and isopropyl acetate; hydrocarbons such as hexane and heptane; aromatic hydrocarbons such as toluene and xylene; ketones such as acetone and 2-butanone; halogenated hydrocarbons such as dichloromethane and chloroform; halogenated aromatic hydrocarbons such as chlorobenzene; nitriles such as acetonitrile and propionitrile; amides such as N,N-dimethylformamide and N-methylpyrrolidone; and mixtures of any of these solvents. In a preferred embodiment, the solvent is a halogenated hydrocarbon or a nitrile, more preferably a halogenated hydrocarbon such as dichloromethane or chloroform, and most preferably dichloromethane.

The reaction may be performed at a temperature between about 0° C. and the boiling point of the reaction solvent. The reaction is preferably performed at a temperature of about 10° C. or higher, most preferably at a temperature of about 15° C. to about 35° C.

Once the reaction is completed, the mixture may be consecutively washed with an aqueous solution of an acid (e.g., an aqueous solution of hydrochloric acid), water, an aqueous solution of a base (e.g., an aqueous solution of sodium hydrogen carbonate) and water, and the solvent may be evaporated. The product may thereafter be further purified, such as by crystallization. The compound of formula (IV) is preferably crystallized from acetonitrile or heptane, and most preferably from acetonitrile. In a most preferred embodiment, the compound of formula (IV) is recrystallized twice from acetonitrile.

In the second step, the compound of formula (IV) is deprotected by hydrolysis of the group $C(O)OR^6$, and preferably by acid hydrolysis of said group. The hydrolysis can be performed in the presence of a suitable acid and results in the corresponding carboxylic acid of formula (I).

Examples of suitable acids include, but are not limited to, hydrochloric acid, sulfuric acid, nitric acid, methanesulfonic acid, p-toluenesulfonic acid, camphorsulfonic acid, benzenesulfonic acid, formic acid, acetic acid and trifluoroacetic acid. In a preferred embodiment, the acid is trifluoroacetic acid.

Suitable solvents for the hydrolysis reaction include ethers such as tetrahydrofuran, dioxane, cyclopentyl methyl ether and 1,2-dimethoxyethane; esters such as ethyl acetate and isopropyl acetate; hydrocarbons such as hexane and heptane; aromatic hydrocarbons such as toluene and xylene; halogenated hydrocarbons such as dichloromethane and chloroform; halogenated aromatic hydrocarbons such as chlorobenzene; nitriles such as acetonitrile and propionitrile; amides such as N,N-dimethylformamide and N-methylpyrrolidone; and mixtures of any of these solvents. In a preferred embodiment, the solvent is an aromatic hydrocarbon, more preferably an aromatic hydrocarbon such as toluene or xylene, and most preferably toluene.

The reaction may be performed at a temperature between about 0° C. and the boiling point of the reaction solvent. The reaction is preferably performed at a temperature of about 15° C. to about 35° C.

Once the hydrolysis is completed, the acid may be removed by washing with water and the organic solvent may be evaporated. The product may thereafter be further purified, such as by crystallization or precipitation. The compound of formula (I) is preferably crystallized from ethanol, or precipitated from a solution by the addition of heptane, in particular n-heptane.

In a further embodiment of invention, the compound of formula (II) is prepared by an alkylation reaction comprising reacting a compound of formula (V):

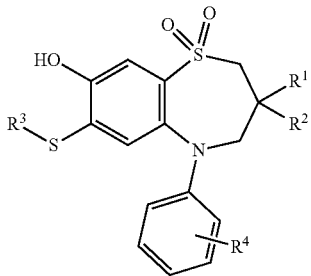

(V)

wherein $R^1$ to $R^4$ are as defined above
with a compound of formula (VI):

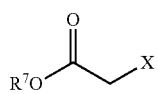

(VI)

wherein
$R^7$ is a suitable protecting group; and
X is a suitable leaving group;
to obtain an intermediate compound of formula (VII):

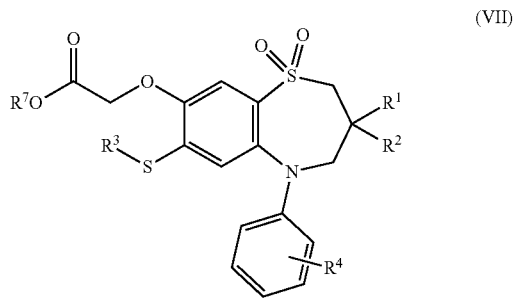

(VII)

followed by hydrolysis of the ester $R^7O$—$C(O)$—,
to obtain the compound of formula (II).

In the alkylating agent of formula (VI), $R^7$ is preferably selected from the group consisting of $C_{1-4}$ alkyl and $C_{1-4}$ haloalkyl. More preferably, $R^7$ is $C_{1-4}$ alkyl such as methyl, ethyl or tert-butyl, and most preferably $R^7$ is ethyl. X is preferably selected from the group consisting of halo, trifluoromethanesulfonate, methanesulfonyl and p-toluenesulfonyl. More preferably, X is halogen, and more preferably a halogen selected from chloride, bromide and iodide. In a most preferred embodiment, the compound of formula (VI) is ethyl bromoacetate.

The compound of formula (VI) may be used in slight excess with respect to the compound of formula (V). The best yields may be obtained if the compound of formula (VI) is used in about 1.1 to about 1.4 equivalents with respect to the compound of formula (V).

The alkylation reaction between compounds of formulas (V) and (VI) is preferably performed in the presence of a phase transfer catalyst and a base. Examples of suitable phase transfer catalysts include tetra-n-butylammonium bromide (TBAB), benzyltrimethylammonium chloride, benzyltriethylammonium chloride, methyltricaprylammonium chloride, methyltributylammonium chloride and methyltrioctylammonium chloride. Tetra-n-butylammonium bromide is most preferred. Examples of suitable bases include metal hydroxides such as sodium hydroxide, potassium hydroxide and lithium hydroxide; metal carbonates such as sodium carbonate, potassium carbonate and lithium carbonate; and metal hydrogen carbonates such as sodium hydrogen carbonate, potassium hydrogen carbonate and lithium hydrogen carbonate. In a preferred embodiment, the base is a metal carbonate, most preferably sodium carbonate. The base may be used in excess of the compound of formula (VI), preferably in an amount of about 3.0 to about 6.0 equivalents, and more preferably in an amount of about 3.5 to about 4.0 equivalents with respect to the compound of formula (VI).

Suitable solvents for the alkylation reaction include ethers such as tetrahydrofuran, dioxane, cyclopentyl methyl ether and 1,2-dimethoxyethane; esters such as ethyl acetate and isopropyl acetate; hydrocarbons such as hexane and heptane; aromatic hydrocarbons such as toluene and xylene; ketones such as acetone and 2-butanone; halogenated hydrocarbons such as dichloromethane and chloroform; halogenated aromatic hydrocarbons such as chlorobenzene; nitriles such as acetonitrile and propionitrile; and amides such as N,N-dimethylformamide and N-methylpyrrolidone; and mixtures of any of these solvents. In a preferred embodiment, the solvent is an aromatic hydrocarbon or a halogenated hydrocarbon, more preferably toluene or xylene, and most preferably toluene.

The reaction may be performed at a temperature between about 0° C. and the boiling point of the reaction solvent. The reaction is preferably performed at a temperature of about 20° C. or higher, and most preferably at a temperature of about 75° C. to about 85° C., especially when using aromatic hydrocarbons as the solvent.

Once the alkylation reaction is completed, water may be added and the phase transfer catalyst and the base extracted to the aqueous layer. The intermediate compound of formula (VII) may then be isolated and further purified. It has been found that at least when using aromatic hydrocarbons as the solvent, the compound of formula (VII) is obtained in high yields and with high purity. In such cases, the intermediate compound of formula (VII) may immediately be used in the next step without further isolation and purification. In a preferred embodiment, therefore, the intermediate compound of formula (VII) is not isolated but used immediately in the next step.

In said next step, the compound of formula (VII) is hydrolyzed, preferably under basic conditions, resulting in a compound of formula (II). The hydrolysis may be performed in an organic solvent, to which an aqueous solution of a base is added.

Examples of suitable bases include metal hydroxides such as sodium hydroxide, potassium hydroxide and lithium hydroxide; metal carbonates such as sodium carbonate, potassium carbonate and lithium carbonate; and metal hydrogen carbonates such as sodium hydrogen carbonate, potassium hydrogen carbonate and lithium hydrogen carbonate. In a preferred embodiment, the base is a metal hydroxide, most preferably sodium hydroxide. The base is preferably used in excess of the compound of formula (VII), preferably in an amount of about 2.0 to about 6.0 equivalents, more preferably in an amount of about 3.0 to about 5.0 equivalents and more preferably in an amount of about 3.5 to about 4.5 equivalents with respect to the compound of formula (VII).

Suitable solvents for the hydrolysis reaction include alcohols such as methanol, ethanol, n-propanol, isopropanol, n-butanol and t-butanol; ethers such as tetrahydrofuran, dioxane, cyclopentyl methyl ether and 1,2-dimethoxyethane; hydrocarbons such as hexane and heptane; aromatic hydrocarbons such as toluene and xylene; ketones such as acetone and 2-butanone; halogenated hydrocarbons such as dichloromethane and chloroform; halogenated aromatic hydrocarbons such as chlorobenzene; and mixtures of any of these solvents. In a preferred embodiment, the solvent is an alcohol or an aromatic hydrocarbon, more preferably an aromatic hydrocarbon such as toluene or xylene, and most preferably toluene.

It is especially advantageous if the same solvent is used during the alkylation and the subsequent hydrolysis reaction.

The reaction may be performed at a temperature between about 0° C. and the boiling point of the reaction solvent. The reaction is preferably performed at a temperature of about 20° C. or higher, most preferably at a temperature of about 45° C. to about 55° C. when aromatic hydrocarbons are used as the solvent or at a temperature of about 20° C. to about 30° C. when alcohols are used as the solvent.

Once the hydrolysis reaction is completed, the reaction mixture may be acidified by addition of an acid, such as formic acid, and the organic layer may be washed and concentrated. The reaction product may thereafter be further purified. Both the compound of formula (II) and the corresponding sodium salt may be precipitated or crystallized from an organic solvent. Therefore, in a preferred embodiment of the invention, the compound of formula (II) is first crystallized as the corresponding sodium salt and thereafter protonated and crystallized as the parent compound. In some embodiments, crystallizing the compound of formula (II) as the corresponding sodium salt removes any non-salt organic impurities. The sodium salt of the compound of formula (II) is preferably crystallized from a mixture of ethyl acetate and aqueous sodium hydroxide, and the compound of formula (II) is preferably crystallized from a mixture of ethyl acetate and n-heptane.

In a further embodiment of the invention, the process also comprises transforming the compound of formula (I) into a stable crystalline hydrate of formula (I). This may be achieved by recrystallizing the compound of formula (I) from ethanol, or from a solvent mixture comprising ethanol and one or more other suitable solvents. In a preferred embodiment, the compound of formula (I) is elobixibat and the stable crystalline hydrate of formula (I) is a crystalline monohydrate of elobixibat, most preferably crystal modification IV of elobixibat (also referred to as crystal form IV of elobixibat).

It has previously been disclosed that crystal modification IV can be obtained by crystallizing crude elobixibat from ethanol, or from a mixture of ethanol and water. Under such conditions, a crystalline ethanolate of elobixibat is initially formed, which may be isolated and dried. Drying of the crystalline ethanolate results in an anhydrate, which quickly absorbs moisture from the air, thereby turning into crystal modification IV of elobixibat. It has now been found that improved results are obtained when crude elobixibat is dissolved in a mixture of ethanol and ethyl acetate. As elobixibat is fully soluble in this solvent mixture, additional filtration steps of the resulting solution may be performed in order to remove any foreign particles or microorganisms. Improved results may also be obtained if n-heptane is added to the solution of the compound of formula (I) in the mixture of ethanol and ethyl acetate.

In a second aspect, the invention relates to a process for the preparation of crystal modification IV of elobixibat, comprising the steps of:
(i) dissolving crude elobixibat in a mixture of ethanol and ethyl acetate;
(ii) crystallizing a crystalline ethanolate of elobixibat from the solution of crude elobixibat in the mixture of ethanol and ethyl acetate obtained in step (i);
(iii) drying the crystalline ethanolate of elobixibat to obtain a crystalline anhydrate of elobixibat; and
(iv) hydrating the crystalline anhydrate of elobixibat to obtain crystal modification IV of elobixibat.

Crystal modification IV of elobixibat may have an X-ray powder diffraction (XRPD) pattern, obtained with CuKα1-radiation, with at least specific peaks at °2θ positions 6.3±0.2 and/or 19.4±0.2.

In one embodiment, crystal modification IV of elobixibat may have an X-ray powder diffraction (XRPD) pattern, obtained with CuKα1-radiation, with specific peaks at °2θ positions 6.3±0.2 and 19.4±0.2 and one or more of the characteristic peaks: 10.2±0.2, 10.5±0.2, 9.4±0.2, 9.5±0.2, 12.5±0.2, 14.6±0.2, 15.6±0.2 and 23.3±0.2.

In another embodiment, crystal modification IV of elobixibat may have an X-ray powder diffraction (XRPD) pattern, obtained with CuKα1-radiation, with specific peaks at °2θ positions 6.3±0.2, 19.4±0.2, 10.2±0.2, 10.5±0.2, 9.4±0.2 and 9.5±0.2.

In another embodiment, crystal modification IV of elobixibat may have an X-ray powder diffraction (XRPD) pattern, obtained with CuKα1-radiation, with characteristic peaks at °2θ positions 6.3±0.2, 19.4±0.2, 10.2±0.2, 10.5±0.2, 9.4±0.2, 9.5±0.2, 12.5±0.2, 14.6±0.2, 15.6±0.2 and 23.3±0.2, and one or more of 8.3±0.2, 11.3±0.2, 13.4±0.2, 13.9±0.2, 16.3±0.2, 16.6±0.2, 18.2±0.2, 18.8±0.2, 19.1±0.2, 19.3±0.2, 19.7±0.2, 19.8±0.2, 20.5±0.2, 21.0±0.2, 21.3±0.2, 21.4±0.2, 22.6±0.2, 22.9±0.2, 23.1±0.2, 23.9±0.2, 24.5±0.2, 24.7±0.2, 25.0±0.2, 25.2±0.2, 25.4±0.2, 25.7±0.2, 26.7±0.2, 26.9±0.2, 28.3±0.2 and 28.9±0.2.

In another embodiment, the crystal modification IV of elobixibat may have an X-ray powder diffraction (XRPD) pattern, obtained with CuKα1-radiation, with characteristic peaks at °2θ positions 6.3±0.2, 8.3±0.2, 9.4±0.2, 9.5±0.2, 10.2±0.2, 10.5±0.2, 11.3±0.2, 12.5±0.2, 13.4±0.2, 13.9±0.2, 14.6±0.2, 15.6±0.2, 16.3±0.2, 16.6±0.2, 18.2±0.2, 18.8±0.2, 19.1±0.2, 19.3±0.2, 19.4±0.2, 19.7±0.2, 19.8±0.2, 20.5±0.2, 21.0±0.2, 21.3±0.2, 21.4±0.2, 22.6±0.2, 22.9±0.2, 23.1±0.2, 23.3±0.2, 23.9±0.2, 24.5±0.2, 24.7±0.2, 25.0±0.2, 25.2±0.2, 25.4±0.2, 25.7±0.2, 26.7±0.2, 26.9±0.2, 28.3±0.2 and 28.9±0.2.

The mixture of ethanol and ethyl acetate wherein crude elobixibat is dissolved may be a 10:1 to 0.5:1 mixture (w/w) of ethanol and ethyl acetate. In a preferred embodiment, crude elobixibat is dissolved in a mixture of about 1.85:1 (w/w) of ethanol and ethyl acetate.

In one embodiment, the crystallization in step (ii) is initiated by the addition of a seed crystal of crystal modification IV of elobixibat to the solution of crude elobixibat in a mixture of ethanol and ethyl acetate.

In another embodiment, n-heptane is added in step (ii) to the solution of crude elobixibat in the mixture of ethanol and ethyl acetate.

The invention disclosed herein has several advantages. The claimed process for the preparation of elobixibat comprises fewer steps than previously disclosed processes and is therefore more efficient and cost-efficient. It also allows elobixibat to be isolated in higher yields and with lower impurity levels. The process comprises improved purification steps and eliminates the need for several chromatography steps, which are not suitable for use in large-scale synthesis. The process furthermore involves an improvement in the preparation of crystal modification IV of elobixibat. Overall, the process allows elobixibat (or a stable crystalline monohydrate thereof) to be prepared on an industrial scale.

The compounds of formula (I) are ileal bile acid transporter (IBAT) inhibitors. They are therefore useful in the treatment or prevention of conditions, disorders and diseases wherein inhibition of the bile acid circulation is desirable, such as fatty acid metabolism and glucose utilization disorders, gastrointestinal diseases and disorders and liver diseases and disorders.

Disorders of fatty acid metabolism and glucose utilization include, but are not limited to, hypercholesterolemia, dyslipidemia, metabolic syndrome, obesity, disorders of fatty acid metabolism, glucose utilization disorders, disorders in which insulin resistance is involved, and type 1 and type 2 diabetes mellitus.

Gastrointestinal diseases and disorders include constipation (including chronic constipation, functional constipation, chronic idiopathic constipation (CIC) and constipation predominant irritable bowel syndrome (IBS-C)); Crohn's disease; primary bile acid malabsorption; irritable bowel syndrome (IBS); inflammatory bowel disease (IBD); ileal inflammation; and reflux disease and complications thereof.

A liver disease as defined herein is any bile acid-dependent disease in the liver and in organs connected therewith, such as the pancreas, portal vein, the liver parenchyma, the intrahepatic biliary tree, the extrahepatic biliary tree, and the gall bladder. Liver diseases and disorders include, but are not limited to an inherited metabolic disorder of the liver; inborn errors of bile acid synthesis; congenital bile duct anomalies; biliary atresia; post-Kasai biliary atresia; post-liver transplantation biliary atresia; neonatal hepatitis; neonatal cholestasis; hereditary forms of cholestasis; cerebrotendinous xanthomatosis; a secondary defect of BA synthesis; Zellweger's syndrome; cystic fibrosis (manifestations in the liver); alpha1-antitrypsin deficiency; Alagilles syndrome (ALGS); Byler syndrome; a primary defect of bile acid (BA) synthesis; progressive familial intrahepatic cholestasis (PFIC) including PFIC-1, PFIC-2, PFIC-3 and non-specified PFIC, post-biliary diversion PFIC and post-liver transplant PFIC; benign recurrent intrahepatic cholestasis (BRIC) including BRIC1, BRIC2 and non-specified BRIC, post-biliary diversion BRIC and post-liver transplant BRIC; autoimmune hepatitis; primary biliary cirrhosis (PBC); liver fibrosis; non-alcoholic fatty liver disease (NAFLD); non-alcoholic steatohepatitis (NASH); portal hypertension; general cholestasis; jaundice during pregnancy; jaundice due to drugs; intrahepatic cholestasis; extrahepatic cholestasis; primary sclerosing cholangitis (PSC); gall stones and choledocholithiasis; malignancy causing obstruction of the biliary tree; pruritus due to cholestasis or jaundice; pancreatitis; chronic autoimmune liver disease leading to progressive cholestasis; hepatic steatosis; alcoholic hepatitis; acute fatty liver; fatty liver of pregnancy; drug-induced hepatitis; iron overload disorders; hepatic fibrosis; hepatic cirrhosis; amyloidosis; viral hepatitis (including hepatitis A, hepatitis B, hepatitis C, hepatitis D and hepatitis E); hepatocellular carcinoma (hepatoma); and problems in relation to cholestasis due to tumours and neoplasms of the liver, of the biliary tract and of the pancreas.

In a further aspect, the invention relates to a pharmaceutical composition comprising a compound of formula (I) prepared by the process disclosed herein, in association with one or more pharmaceutically acceptable excipients. The excipients may include fillers, binders, disintegrants, glidants and lubricants. In a preferred embodiment, the compound of formula (I) prepared by the process disclosed herein is elobixibat.

As used herein, the term "pharmaceutically acceptable" refers to those compounds and materials that are suitable for human pharmaceutical use and that are generally safe, non-toxic and neither biologically nor otherwise undesirable.

The pharmaceutical composition may be in a form that is suitable for oral administration, for parenteral injection (including intravenous, subcutaneous, intramuscular and intravascular injection), for topical administration or for rectal administration. In a preferred embodiment, the pharmaceutical composition is in a form that is suitable for oral administration, such as a tablet or a capsule.

Examples of suitable fillers include, but are not limited to, dicalcium phosphate dihydrate, calcium sulfate, lactose (such as lactose monohydrate), sucrose, mannitol, sorbitol, cellulose, microcrystalline cellulose, dry starch, hydrolyzed starches and pregelatinized starch. In certain embodiments, the filler is mannitol and/or microcrystalline cellulose.

Examples of suitable binders include, but are not limited to, starch, pregelatinized starch, gelatin, sugars (such as sucrose, glucose, dextrose, lactose and sorbitol), polyethylene glycol, waxes, natural and synthetic gums (such as acacia gum and tragacanth gum), sodium alginate, cellulose derivatives (such as hydroxypropylmethylcellulose (or hypromellose), hydroxypropylcellulose and ethylcellulose) and synthetic polymers (such as acrylic acid and methacrylic acid copolymers, methacrylic acid copolymers, methyl methacrylate copolymers, aminoalkyl methacrylate copolymers, polyacrylic acid/polymethacrylic acid copolymers and polyvinylpyrrolidone (povidone)). In certain embodiments, the binder is hydroxypropylmethylcellulose (hypromellose).

Examples of suitable disintegrants include, but are not limited to, dry starch, modified starch (such as (partially) pregelatinized starch, sodium starch glycolate and sodium carboxymethyl starch), alginic acid, cellulose derivatives (such as sodium carboxymethylcellulose, hydroxypropyl cellulose, and low substituted hydroxypropyl cellulose (L-HPC)) and cross-linked polymers (such as carmellose, croscarmellose sodium, carmellose calcium and cross-linked PVP (crospovidone)). In certain embodiments, the disintegrant is croscarmellose sodium.

Examples of suitable glidants and lubricants include, but are not limited to, talc, magnesium stearate, calcium stearate, stearic acid, glyceryl behenate, colloidal silica, aqueous silicon dioxide, synthetic magnesium silicate, fine granulated silicon oxide, starch, sodium lauryl sulfate, boric acid, magnesium oxide, waxes (such as carnauba wax), hydrogenated oil, polyethylene glycol, sodium benzoate, polyethylene glycol, and mineral oil. In certain embodiments, the glidant or lubricant is magnesium stearate or colloidal silica.

The pharmaceutical composition may be conventionally coated with one or more coating layers. Enteric coating layers or coating layers for delayed or targeted release of the compound of formula (I) are also contemplated. The coating layers may comprise one or more coating agents, and may optionally comprise plasticizers and/or pigments (or colorants).

Example of suitable coating agents include, but are not limited to, cellulose-based polymers (such as ethylcellulose, hydroxypropylmethylcellulose (or hypromellose), hydroxypropylcellulose, cellulose acetate phthalate, cellulose acetate succinate, hydroxypropyl methylcellulose acetate succinate and hydroxypropyl methylcellulose phthalate), vinyl-based polymers (such as polyvinyl alcohol) and polymers based on acrylic acid and derivatives thereof (such as acrylic acid and methacrylic acid copolymers, methacrylic acid copolymers, methyl methacrylate copolymers, aminoalkyl methacrylate copolymers, polyacrylic acid/polymethacrylic acid copolymers). In certain embodiments, the coating agent is hydroxypropylmethylcellulose. In other embodiments, the coating agent is polyvinyl alcohol.

Examples of suitable plasticizers include, but are not limited to, triethyl citrate, glyceryl triacetate, tributyl citrate, diethyl phthalate, acetyl tributyl citrate, dibutyl phthalate, dibutyl sebacate and polyethylene glycol. In certain embodiments, the plasticizer is polyethylene glycol.

Examples of suitable pigments include, but are not limited to, titanium dioxide, iron oxides (such as yellow, brown, red or black iron oxides) and barium sulfate.

Examples of pharmaceutical compositions comprising a compound of formula (I), particularly elobixibat, are disclosed in e.g., WO 2014/174066, US 2017/0143738 and US 2017/0143783, which are incorporated herein by reference in their entirety.

The dosage required for the treatment or prevention of conditions recited herein will depend on the route of administration, the severity of the disease, the age and weight of the patient and other factors normally considered by the attending physician, when determining the appropriate regimen and dosage level for a particular patient.

The amount of the compound to be administered will vary for the patient being treated, and may vary from about 1 µg/kg of body weight to about 50 mg/kg of body weight per day. A unit dose form, such as a tablet or capsule, will usually contain about 1 to about 250 mg of active ingredient, such as about 1 to about 100 mg, or such as about 1 to about 50 mg, or such as about 1 to about 20 mg, e.g. about 2.5 mg, or about 5 mg, or about 10 mg, or about 15 mg. The daily dose can be administered as a single dose or divided into one, two, three or more unit doses. An orally administered daily dose of an IBAT inhibitor is preferably within about 0.1 to about 250 mg, more preferably within about 1 to about 100 mg, such as within about 1 to about 5 mg, such as within about 1 to about 10 mg, such as within about 1 to about 15 mg, or such as within about 1 to about 20 mg.

In a further aspect, the invention relates to a method of treating or preventing any of the diseases recited herein in a subject, such as man, comprising administering to the subject in need of such treatment or prevention a therapeutically effective amount of a pharmaceutical composition comprising a compound of formula (I) prepared by the process disclosed herein. The invention also relates to a pharmaceutical composition comprising a compound of formula (I) prepared by the process disclosed herein, for use in the treatment or prevention of any of the diseases recited herein.

The invention also relates to the use of a compound of formula (I) prepared by the process disclosed herein, in the manufacture of a medicament for the treatment or prevention of any of the diseases recited herein. In a preferred embodiment of this aspect, the compound of formula (I) prepared by the process disclosed herein is elobixibat.

The invention is further illustrated by means of the following examples, which do not limit the invention in any respect.

Experimental Methods

General Methods

The reagents and starting materials for the following examples are either commercially available or may be prepared by standard methods known in the art. The starting materials 3,3-dibutyl-7-(methylsulfanyl)-1,1-dioxo-5-phenyl-2,3,4,5-tetrahydro-1H-1,5-benzothiazepin-8-ol and 1,1-dimethylethyl 2-[(2R)-2-benzyloxycarbamido-2-phenylacetamido]acetate may be prepared as described in WO 02/50051 (see methods 26 and 85, respectively).

High resolution mass spectroscopy (HRMS) was performed on a Waters Acquity H Class UPLC/Xevo G2-XS QTof.

EXAMPLES

Example 1

Preparation of {[3,3-dibutyl-7-(methylsulfanyl)-1,1-dioxido-5-phenyl-2,3,4,5-tetrahydro-1,5-benzothiazepin-8-yl]oxy}acetic acid

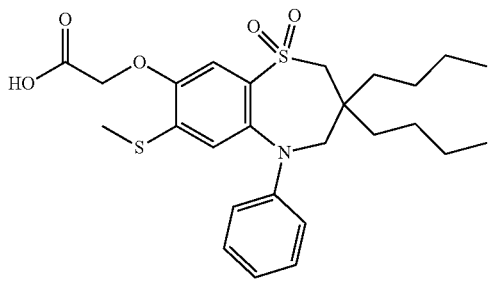 [SMILES: CCCCC1(CCCC)CN(c2ccccc2)c2cc(SC)c(OCC(=O)O)cc2S(=O)(=O)C1]

In a reactor, 3,3-dibutyl-7-(methylsulfanyl)-1,1-dioxo-5-phenyl-2,3,4,5-tetrahydro-1H-1,5-benzothiazepin-8-ol (70.00 kg), sodium carbonate (69.30 kg), tetrabutylammonium bromide (4.55 kg), toluene (606.20 kg), and ethyl bromoacetate (30.10 kg) were mixed and stirred at 80° C. for 4 hrs. After cooling, the reaction mass was washed with water (1680 kg), and the aqueous layer was discarded.

Sodium hydroxide solution (a mixture of 25.04 kg of sodium hydroxide and 225.4 kg of water) was added to the above toluene layer. This mixture was stirred at 47° C. for 3.5 hrs. After cooling, ethyl acetate (374.74 kg) was added to this reaction solution, and thereafter formic acid was added while stirring until the pH became 3.6. The aqueous layer was discarded and the organic layer was washed with water (2×333.84 kg).

The organic layer was concentrated under vacuum and ethyl acetate (599.24 kg) was added to the concentrated residue. After cooling down, sodium hydroxide solution (a mixture of 125.19 kg of sodium hydroxide and 709.41 kg of water) was slowly added while stirring. Crystals of the sodium salt precipitated and were thereafter isolated by centrifugation.

The sodium salt, ethyl acetate (599.24 kg) and water (333.8 kg) were mixed. Formic acid was added while stirring until the pH became 3.5. The organic layer was washed with water (333.8 kg×2) and concentrated under vacuum. n-Heptane (228.68 kg) was added to the concentrated residue and the mixture was stirred. The precipitated crystal was filtered and dried at under vacuum to obtain dry crystal of the title compound as off-white solid (65.38 kg).

HRMS (ESI, m/z) Calcd For $C_{26}H_{34}NO_5S_2$ [M−H]⁻: 504.1880. Found: 504.1832.

Example 2

Preparation of tert-butyl-N-[(2R)-2-amino-2-phenylacetyl] glycinate

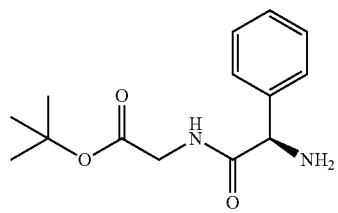 [SMILES: CC(C)(C)OC(=O)CNC(=O)[C@H](N)c1ccccc1]

In a reactor, absolute alcohol (266.30 kg), tert-butyl 2-[(2R)-2-benzyloxycarbamido-2-phenylacetamido]acetate (33.75 kg), 10% palladium on carbon (containing 50% water) (4.05 kg), and toluene (87.75 kg) were mixed. This mixture was stirred at 18° C. under hydrogen at a pressure of 3.5 kg/cm² for 3 hrs.

The reaction mass was filtered and the filter bed was washed with absolute ethanol (106.65 kg). The filtrate was concentrated under vacuum and the title compound was obtained as a colourless viscous liquid (21.70 kg).

HRMS (ESI, m/z) Calcd For $C_{14}H_{21}N_2O_3$ [M+H]⁺: 265.1553. Found: 265.1452.

Example 3

Preparation of tert-butyl-N-{(2R)-2-[({[3,3-dibutyl-7-(methylthio)-1,1-dioxido-5-phenyl-2,3,4,5-tetrahydro-1,5-benzothiazepin-8-yl]oxy}acetyl)amino]-2-phenylethanoyl}glycinate

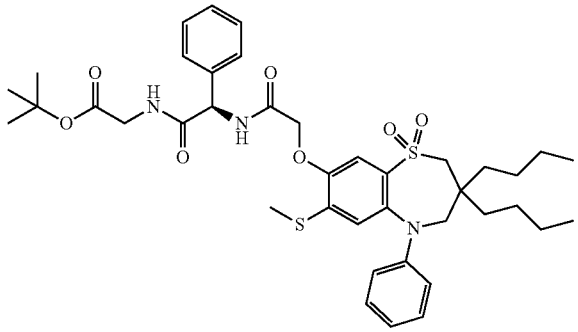 [SMILES: CCCCC1(CCCC)CN(c2ccccc2)c2cc(SC)c(OCC(=O)N[C@@H](C(=O)NCC(=O)OC(C)(C)C)c3ccccc3)cc2S(=O)(=O)C1]

In a reactor, the compound of Example 1 (65.00 kg), the compound of Example 2 (40.95 kg), and dichloromethane (864.50 kg) were mixed. 2,6-Lutidine (37.05 kg) was added and then O-(benzotriazole-1-yl)-N,N,N',N'-tetramethyluronium tetrafluoroborate (46.15 kg) was added at 5° C. This mixture was stirred at 25° C. for 15 hrs. Dichloromethane (1037.40 kg) was added and the organic layer was washed with the following liquids in a sequential order: (1) dilute hydrochloric acid (a mixture of 74.10 kg of hydrochloric acid and 667.55 kg of water); (2) water (260.00 kg); (3) sodium bicarbonate solution (a mixture of 26.00 kg of sodium hydrogen carbonate and 260.00 kg of water); and (4) water (260.00 kg).

The organic layer was concentrated under vacuum. After adding acetonitrile (306.80 kg), the mixture was heated until it dissolved, and then cooled down to 13° C. Crystals precipitated which were then centrifuged and washed with acetonitrile (51.35 kg).

Acetonitrile (606.45 kg) was added to the whole amount of the crude crystal obtained. The mixture was heated until it dissolved, and then cooled down to 0° C. Crystals precipitated, which were centrifuged and washed with acetonitrile (51.35 kg). The wet crystals were vacuum-dried to obtain the title compound as a white powder (81.20 kg).

HRMS (ESI, m/z) Calcd For $C_{40}H_{52}N_3O_7S_2$ [M−H]⁻: 750.3250. Found: 750.3164.

Example 4

Preparation of Crude Elobixibat

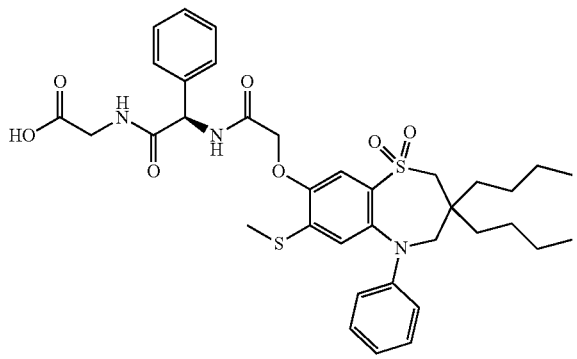 [SMILES: CCCCC1(CCCC)CN(c2ccccc2)c2cc(SC)c(OCC(=O)N[C@@H](C(=O)NCC(=O)O)c3ccccc3)cc2S(=O)(=O)C1]

In a reactor, toluene (1331.10 kg) and the compound of Example 3 (76.50 kg) were mixed. Trifluoro-acetic acid (341.95 kg) was added at 3° C. and the mixture was stirred at 25° C. for 29 hrs. The reaction mixture was repeatedly washed with water (306.00 kg) until the pH of the aqueous layer became 3.4. After the organic layer was filtered, the filtrate was concentrated under vacuum. n-Heptane (520.20 kg) was added to the concentrated residue and the mixture was stirred. The precipitated crystals were centrifuged and washed with n-heptane (104.04 kg). The crystals were vacuum-dried to obtain crude elobixibat as an off-white solid (64.34 kg).

HRMS (ESI, m/z) Calcd For $C_{36}H_{44}N_3O_7S_2$ [M−H]⁻: 694.2623. Found: 694.2553.

Example 5

Preparation of Crystal Modification IV of Elobixibat

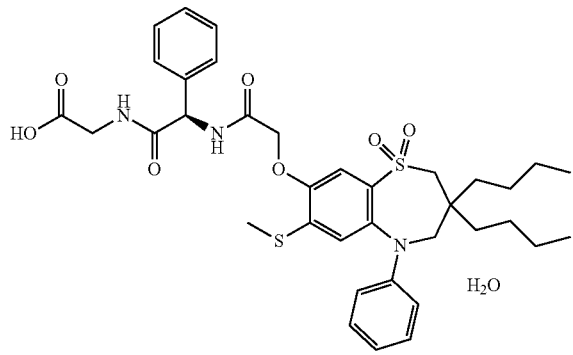 [SMILES: CCCCC1(CCCC)CN(c2ccccc2)c2cc(SC)c(OCC(=O)N[C@@H](C(=O)NCC(=O)O)c3ccccc3)cc2S(=O)(=O)C1 ; O]

Crude elobixibat (64.00 kg), ethyl acetate (154.88 kg), and absolute alcohol (288.00 kg) were mixed in a reactor and the mixture was stirred at 40° C. until it dissolved. After the solution was filtered, the filtrate was washed with a mixture of ethyl acetate (17.28 kg) and absolute alcohol (15.36 kg).

After the filtered solution was cooled down, seed crystals of crystal modification IV of elobixibat (0.032 kg) were added at 25° C. and the mixture was stirred for 2 hrs. n-Heptane (832.00 kg) was added and the mixture continued to be stirred at 23° C. Crystals precipitated which were centrifuged and washed with n-heptane (43.52 kg). The wet crystals were dried under vacuum to obtain dry crystals.

The dried crystals were thereafter hydrated (moistened) by exposing them to humid conditions (40±25% RH) at 25° C. until achieving a water content of 2.4% to 3.4% (as determined by Karl Fischer titration). Crystal modification IV of elobixibat was obtained as a white powder (50.64 kg).

The invention claimed is:

1. A process for the preparation of a compound of formula (I):

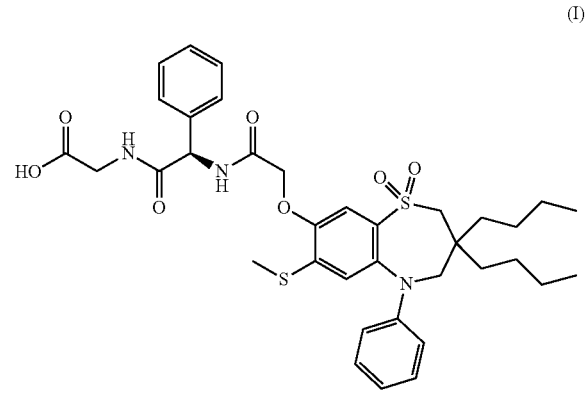 [SMILES: CCCCC1(CCCC)CN(c2ccccc2)c2cc(SC)c(OCC(=O)N[C@@H](C(=O)NCC(=O)O)c3ccccc3)cc2S(=O)(=O)C1]

comprising reacting a compound of formula (II):

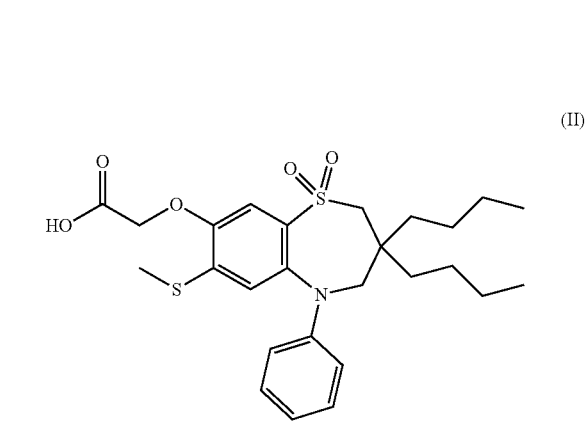 [SMILES: CCCCC1(CCCC)CN(c2ccccc2)c2cc(SC)c(OCC(=O)O)cc2S(=O)(=O)C1]

with a compound of formula (III):

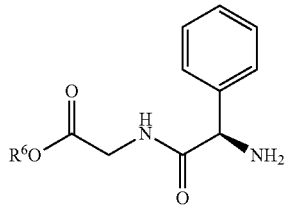

(III)

wherein
R⁶ is a suitable protecting group;
to obtain a compound of formula (IV):

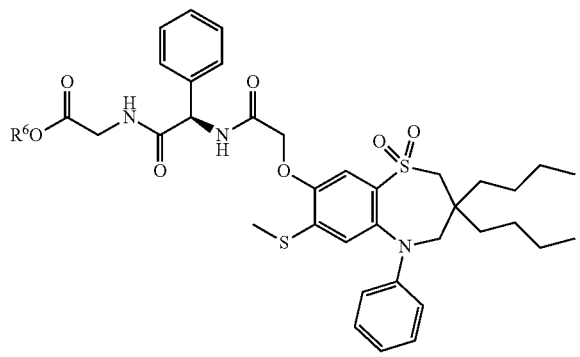

(IV)

and deprotecting said compound of formula (IV) to obtain the compound of formula (I).

2. The process according to claim 1, wherein $R^6$ is selected from the group consisting of $C_{1-4}$ alkyl and trisubstituted silyl.

3. The process according to claim 1, wherein $R^6$ is tert-butyl.

4. The process according to claim 1, wherein the reaction between the compounds of formulas (II) and (III) is performed in the presence of 2,6-lutidine.

5. The process according to claim 1, wherein the compound of formula (IV) is recrystallized from acetonitrile.

6. The process according to claim 1, wherein the hydrolysis of the compound of formula (IV) is performed in toluene.

7. The process according to claim 1, wherein the compound of formula (I) is precipitated from a solution by the addition of heptane.

8. The process according to claim 1, wherein the compound of formula (II) is prepared by an alkylation reaction comprising reacting a compound of formula (V):

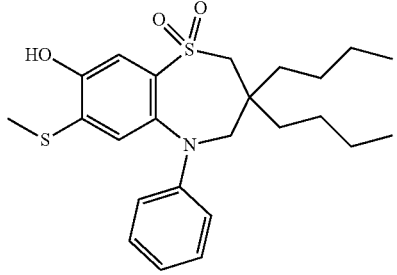

(V)

with a compound of formula (VI):

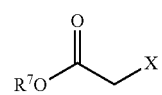

(VI)

wherein
$R^7$ is a suitable protecting group; and
X is a suitable leaving group;
to obtain an intermediate compound of formula (VII):

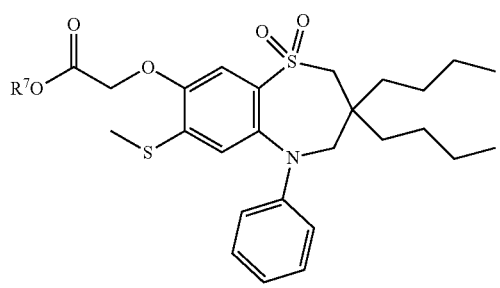

(VII)

followed by hydrolysis of the ester $R^7O—C(O)—$,
to obtain the compound of formula (II).

9. The process according to claim 8, wherein $R^7$ is selected from the group consisting of $C_{1-4}$ alkyl and $C_{1-4}$ haloalkyl.

10. The process according to claim 8, wherein X is selected from the group consisting of halo, trifluoromethanesulfonate, methanesulfonyl and p-toluenesulfonyl.

11. The process according to claim 8, wherein the compound of formula (II) is first precipitated as the corresponding sodium salt and thereafter protonated and crystallized.

12. The process according to claim 8, wherein the preparation of the intermediate compound of formula (VII) is performed in toluene.

13. The process according to claim 8, wherein the intermediate compound of formula (VII) is not isolated but used immediately in the next step.

14. The process according to claim 8, wherein the alkylation reaction and the subsequent hydrolysis reaction are performed in the same solvent.

15. The process according to claim 1, further comprising transforming the compound of formula (I) into a stable crystalline hydrate of formula (I).

16. The process according to claim 15, wherein the compound of formula (I) is dissolved in a mixture of ethanol and ethyl acetate.

17. The process according to claim 15, wherein n-heptane is added to the solution of the compound of formula (I) in the mixture of ethanol and ethyl acetate.

18. The process according to claim 15, wherein the stable crystalline hydrate is a crystalline monohydrate.

19. A process for the preparation of a crystal modification IV of elobixibat, comprising the steps of:
   (i) dissolving crude elobixibat in a mixture of ethanol and ethyl acetate;
   (ii) crystallizing a crystalline ethanolate of elobixibat from the solution of crude elobixibat in the mixture of ethanol and ethyl acetate obtained in step (i);
   (iii) drying the crystalline ethanolate of elobixibat to obtain a crystalline anhydrate of elobixibat; and
   (iv) hydrating the crystalline anhydrate of elobixibat to obtain crystal modification IV of elobixibat.

20. The process according to claim 19, wherein in step (ii) n-heptane is added to the solution of crude elobixibat in the mixture of ethanol and ethyl acetate.

* * * * *